US008874220B2

(12) United States Patent
Draghici et al.

(10) Patent No.: US 8,874,220 B2
(45) Date of Patent: Oct. 28, 2014

(54) NEUROSTIMULATION SYSTEM, DEVICE, AND METHOD

(71) Applicant: NorDocs Technologies Inc., Ottawa (CA)

(72) Inventors: Ovidiu Ioan Draghici, Hull (CA); Izmail Batkin, Ottawa (CA); Miodrag Bolic, Ottawa (CA); Ian Stanley Chapman, Gatineau (CA); Alexey Borisenko, Ottawa (CA); Daniel Shapiro, Ottawa (CA); Stanley Shapiro, Sudbury (CA); Brian Dressler, Sudbury (CA)

(73) Assignee: Nuraleve Inc., Ottawa, ON (CA)

( * ) Notice: Subject to any disclaimer, the term of this patent is extended or adjusted under 35 U.S.C. 154(b) by 0 days.

(21) Appl. No.: 13/713,769

(22) Filed: Dec. 13, 2012

(65) Prior Publication Data

US 2014/0172041 A1 Jun. 19, 2014

(51) Int. Cl.
*A61N 1/05* (2006.01)
*A61N 1/36* (2006.01)

(52) U.S. Cl.
CPC ................................. *A61N 1/36082* (2013.01)
USPC ................ 607/46; 607/45; 607/115; 607/148

(58) Field of Classification Search
CPC . A61N 1/0523; A61N 1/052; A61N 1/36075; A61N 1/36082; A61N 1/36103; A61N 2001/36039; A61N 1/20; A61N 1/32
USPC ....................... 607/1, 2, 115, 148, 45–47, 118
See application file for complete search history.

(56) References Cited

U.S. PATENT DOCUMENTS

| 2,055,540 | A | * | 9/1936 | Karnofsky | 607/134 |
|---|---|---|---|---|---|
| 3,207,161 | A | * | 9/1965 | Dietz | 607/134 |
| 5,540,734 | A | | 7/1996 | Zabara | |
| 6,430,450 | B1 | * | 8/2002 | Bach-y-Rita et al. | 607/134 |
| 7,949,403 | B2 | * | 5/2011 | Palermo et al. | 607/46 |
| 8,290,582 | B2 | * | 10/2012 | Lin et al. | 607/2 |
| 2005/0240253 | A1 | * | 10/2005 | Tyler et al. | 607/134 |
| 2006/0161218 | A1 | | 7/2006 | Danilov | |
| 2006/0241718 | A1 | * | 10/2006 | Tyler et al. | 607/45 |

(Continued)

OTHER PUBLICATIONS

Nitsche, et al.; Transcranial Direct Current Stimulation: State of the Art 2008; Brain Stimulation, (2008), vol. 1, pp. 206-223.

(Continued)

*Primary Examiner* — George Evanisko
(74) *Attorney, Agent, or Firm* — Canpatents, Inc.; Timothy Marc Shropshire

(57) ABSTRACT

A device for cranial nerve stimulation of an individual is disclosed, having a signal driver unit for producing a current; an intraoral stimulation board having at least one primary electrode, and at least one secondary electrode positioned on the individual for communicating a current through the individual, wherein current can flow between the intraoral stimulation board and the secondary electrode. The device may be used to treat a number of ailments. In one embodiment, the device provides input representing two planes of movement, or is used as a gaming controller. A method of using an electrical stimulation system is also disclosed, comprising the steps of: a) positioning the intraoral stimulation board within the individual's mouth; b) connecting the secondary electrode to the individual; c) operating the signal driver unit for a predetermined time to provide a current flow between the intraoral stimulation board and the secondary electrode.

9 Claims, 16 Drawing Sheets

(56) References Cited

U.S. PATENT DOCUMENTS

| | | | |
|---|---|---|---|
| 2008/0009772 A1 | 1/2008 | Tyler et al. | |
| 2008/0082131 A1* | 4/2008 | Llanos | 607/2 |
| 2008/0228239 A1 | 9/2008 | Tyler et al. | |
| 2009/0210032 A1* | 8/2009 | Beiski et al. | 607/59 |
| 2009/0312808 A1 | 12/2009 | Tyler et al. | |
| 2009/0326604 A1 | 12/2009 | Tyler et al. | |
| 2010/0070006 A1* | 3/2010 | Wagner et al. | 607/116 |
| 2011/0093036 A1* | 4/2011 | Mashiach | 607/48 |
| 2011/0178428 A1* | 7/2011 | Messie | 600/582 |

OTHER PUBLICATIONS

Nitsche, et al.; "Transcranial Direct Current Stimulation—Update 2011;" Restorative Neurology and Neuroscience, (2011), vol. 29, pp. 1-30.

Wildenberg, et al.; "Sustained Cortical and Subcortical Neuromodulation Induced by Electrical Tongue Stimulation;" Brain Imaging and Behavior, (2010), vol. 4, pp. 199-211.

NeuroImage; (2011); vol. 56, pp. 2129-2137.

Journal of Rehabilitation Research and Development; vol. 35, No. 4, pp. 427-430 (Oct. 1998).

Fisher, et al.; "Neuroplasticity-Based Cognitive Training in Schizophrenia: An Interim Report on the Effects 6 Months Later;" Schizophrenia Bulletin, pp. 1-11 (Mar. 5, 2009).

Pleasonton; "Sensitivity of the Tongue to Electrical Stimulation;" J. Speech Hear. Res.; (1970), vol. 13, pp. 635-644.

Loucks, et al.; "Effects of Stimulation Duration on Electrogustometric Thresholds;" Physiology & Behavior, (2004), vol. 81, pp. 1-4.

Physiology & Behavior, (2002), vol. 75 pp. 753-757.

Nicolaescu, et al.; "Electrical Taste Thresholds Established on the Medial Tongue using Two Sizes of Electrodes;" The Laryngoscope; vol. 15, pp. 1509-1511 (Aug. 2005).

Neuropsychological Rehabilitation: An International Journal; No. 21, vol. 5, pp. 602-617 (2011).

Danilov, et al.; "Brainport: An Alternative Input to the Brain;" Journal of Integrative Neuroscience; vol. 4, No. 4, pp. 537-550 (2005).

Bach-Y-Rita, et al.; "Seeing with the Brain;" International Journal of Human-Computer Interaction; vol. 15, No. 2, pp. 285-295 (2003).

Frontiers in Human Neuroscience, vol. 4, art. 32, pp. 1-12 (Apr. 2010).

Matsuda, et al.; Regional Taste Sensitivity to NaCl: Relationship to Subject Age, Tongue Locus and Area of Stimulation; Univ. Penn. Med. Center; pp. 283-290 (Nov. 1, 1994).

* cited by examiner

NEUROSTIMULATION SYSTEM, DEVICE, AND METHOD

BACKGROUND OF THE INVENTION

1. Field of the Invention

The invention relates to electrical stimulation of the body, and in particular a system, device and method for controlled and monitored electrical stimulation of the brain, through the afferent cranial nerves linked to the oral cavity.

2. Description of the Prior Art

Brain plasticity or neuroplasticity is the brain's capability of restructuring itself, leading to functional recovery after brain damage. Neuroplasticity can be induced through neurostimulation, also called neuromodulation. Various methods are used to provide neurostimulation, like Cognitive-Behavior Therapy (CBT), Transcranial Magnetic Stimulation (TMS), as well as various types of electrical stimulation, like Transcranial Direct Current Stimulation (tDCS), Transcranial Alternating Current Stimulation (tACS), Transcranial Random Noise Stimulation (tRNS), and Cranial Nerve Non-Invasive Neuromodulation (CN-NINM).

Electrical stimulation has been increasingly used in the last decades, in the rehabilitation of patients suffering from neurological conditions, the most widely used method being tDCS. Electrical stimulation is also used for sensory augmentation and substitution, more specifically for visual or balance impaired individuals. tDCS is a non-invasive method of neuromodulation, known to induce lasting changes in the brain, These neuroplastic changes are achieved by increasing or decreasing the firing rates of the neurons, through the hyperpolarization or depolarization of the resting membrane's potential.

Various devices have been developed recently for the purpose of inducing neuroplasticity non-invasively, through electrical stimulation. Companies like Soterix™, Magstim™, Nexalin™, NeuroConn™, and Mind Alive™ have developed transcranial electrical stimulation devices, while Wicab™ has developed an intraoral stimulation device, the Tongue Display Unit (TDU), for sensory substitution and augmentation, as well as CN-NINM. The TDU delivers an alternative current signal to selected regions of the tongue through an array of intraoral electrodes. This stimulation is used to provide exogenous information cues, and has been shown to induce neuromodulation via the cranial nerves. Cognitive-Behavior Therapy has been found to benefit from the addition of learning-induced neuroplasticity via computerized cognitive training.

A major challenge related to tDCS is the relatively high impedance of the skull and the skin, that limits the current delivered through trans-cutaneous electrodes placed on or near the scalp; only about 50% of the stimulation current is routed through the brain tissue. The higher the impedance, the more difficult is to ensure a focused targeted delivery of current. The TDU, on the other hand, has a different type of problem: it was designed to use saliva to facilitate the delivery of the AC stimulus, thus it is missing the capability to deliver DC stimulus, which requires a physical barrier in order to avoid the deposition of material from the electrode(s) to the human tissue, through electrolysis. The TDU is only delivering stimuli to the surface of the tongue, in particular the tip of the tongue, stimulating only to the cranial nerves connected to these regions. None of these devices are providing feedback regarding the position of the electrode(s) as well as the quality of the contact between electrodes and the tissue.

SUMMARY OF THE PRESENT INVENTION

A programmable electronic platform for neurostimulation and biofeedback, called the Neuro-Electrode ARray (NEAR) is disclosed, along with an electrode array for the tongue. The invention combines two types of electrical stimulation therapies and the respective electrodes and electrode placements, Transcranial Electrical Stimulation and Non-Invasive Cranial Nerve Neuromodulation, as well as a combination of the two, referred to as Cranial Nerve Electrical Stimulation (CNES). The NEAR platform is able to provide electrical stimulation with either alternating (AC), or direct current (DC), or both. By combining both types of stimulation and electrodes, the NEAR platform is able to deliver transcutaneous electrical stimulation to the brain and the body.

This platform is able to overcome the tDCS impedance related problems by placing one of the electrodes intraorally, and thus avoiding the higher impedance of the skin and the skull. The delivery of DC stimulus is facilitated by a removable conductive cover that prevents the deposition of material from electrode(s) into the tissue.

The intraoral placement of the stimulus can vary according to the condition treated, since different cranial nerves are connected to different regions within the oral cavity, like the anterior and posterior tongue, the palate, etc. This is achieved by allowing the placement of the electrode array not only on the tongue, but on the lips, and palate as well, via a retainer.

The platform can read the impedance of the connection between the electrodes and the body, via Analog to Digital Conversion (ADC), by sending a test pulse through the electrodes and measuring the response on the return path. By reading the contact impedance, the device is able to optimize and lock the stimulation signal to a specific position.

A device for cranial nerve stimulation of an individual is disclosed, the device comprising a signal driver unit for producing a current; an intraoral stimulation board having at least one primary electrode, for communicating a current with a tongue of the individual, the intraoral stimulation board connected to the signal driver unit; at least one secondary electrode positioned on the individual for communicating a current through the individual, the electrode connected to the signal driver unit, wherein current can flow between the intraoral stimulation board and the secondary electrode.

In a further embodiment, the device further comprises a cover for the intraoral stimulation board for preventing transmission of electrode materials. The cover may be a partial cover that covers part of the intraoral stimulation device, wherein AC current is provided by the at least one primary electrode that is uncovered, and DC current is communicated by the at least one primary electrode that is covered.

In a further embodiment, the device further comprises a microcontroller connected to the primary and secondary electrodes; a feedback loop between the electrodes and the microcontroller wherein a test signal is sent between the primary and secondary electrodes, which signal is measured by the microcontroller, thus providing feedback regarding the contact between the tissue and the electrode, or the impedance of the tissue at the location of the electrode. The device may further comprise an accelerometer to communicate information on head movement to the microcontroller. The device's microcontroller is capable of determining a tongue position by measuring the impedance between the tongue and electrodes, such that the device may be operated as a touchpad. The device may further comprise sensors that operate as buttons for the touch pad by providing a signal to the microcontroller, and may further comprise predetermined sections of the electrodes, wherein the sections are assigned specific actions.

The use of the device as a touchpad is disclosed is disclosed. The use of the device for diagnosis of oral conditions and for diagnosis of tongue cancer is further disclosed. A method of use of the device for diagnosis of oral conditions by sending a test signal and measuring the response from intraoral stimulation board is also disclosed.

The device may be used for the treatment of a disorder selected from the group consisting of: vestibular balance disorders; aphasia after stroke; motor function impairment after chronic stroke; central pain from traumatic spinal cord injury; working memory and motor function impairment from Parkinson's disease; chronic pain from fibromyalgia; depression and other mood disorders; seizure resulting from focal epilepsy; visual and recognition memory impairment from Alzheimer's disease; chronic neuropathic pain from multiple sclerosis; nicotine addiction; and migraine headaches. In one embodiment, the device provides input representing two and/or three axis of movement, or is used as a gaming controller.

A method of using an electrical stimulation system is disclosed, comprising the steps of: a) positioning the intraoral stimulation board within the individual's mouth; b) connecting the secondary electrode to the individual; c) operating the signal driver unit for a predetermined time to provide a current flow between the intraoral stimulation board and the secondary electrode. In one embodiment, the method further comprises the step of applying tDCS treatment to the individual. Also disclosed is a method for determining the position of an intraoral stimulation board on a tongue, comprising the steps of: a) sending a test pulse; b) receiving a return pulse from each electrode; c) measuring the return pulse from each electrode; and d) determining which electrodes are not in contact with the tongue by applying a range to the measurement of each return pulse.

BRIEF DESCRIPTION OF THE DRAWINGS

The invention, both as to its organization and method of operation, together with further aspects and advantages thereof, may be best understood by reference to the accompanying drawings and text thereof in light of the brief description therefore.

DETAILED DESCRIPTION OF THE PRESENT INVENTION

Figure 1:
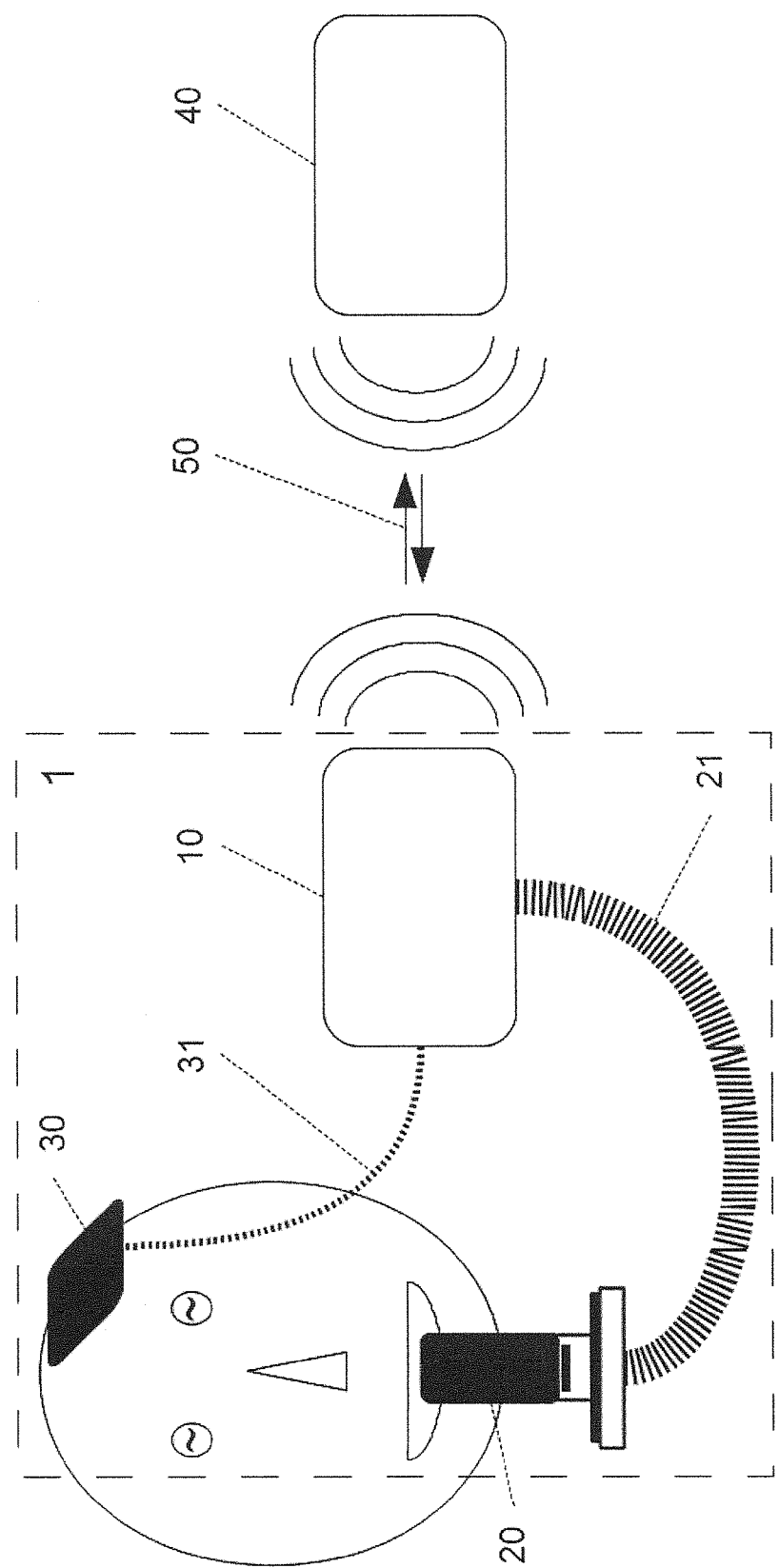
FIG. 1 shows an overview of the NEAR platform.

The present invention will now be described more fully hereinafter with reference to the accompanying drawings, in which preferred embodiments of the present invention are shown. This invention may however, be embodied in many different forms and should not be construed as limited to the embodiments set forth herein. Rather, these embodiments are provided so that this application will be thorough in illustrations and brief explanation therefore to convey the true scope of the invention to those skilled in the art. Some illustrations provided herein include detailed explanations of dimension and operation and as such should be not be limited thereto.

Intraoral electrical stimulation is used to treat vestibular balance disorders, while tDCS is known to alleviate the symptoms of several conditions and improve functions affected by the following exemplary conditions: improved naming (stroke-induced aphasia), motor function recovery (chronic stroke), central pain (traumatic spinal cord injury), working memory enhancement and motor function improvement (Parkinson's), pain amelioration (fibromyalgia), depression and other mood disorders, migraine, seizure reduction (focal epilepsy), visual and recognition memory (Alzheimer), chronic neuropathic pain (multiple sclerosis), and addiction (craving reduction for nicotine and alcohol). The electrical impedance of tongue's tissue can be used in the diagnosis of tongue conditions, including but not limited to tongue cancer. The CNES treatment provided by NEAR is capable of stimulating the brain in a similar way with that of tDCS, therefore examples of tDCS treatment are also applicable to CNES.

The typical tDCS treatment consists of several stimulation sessions, with currents under 4 mA, and a duration of under half an hour; the locations on the scalp for the anode and cathode electrodes are chosen based on the EEG 10/20 system, or by identifying the respective region on the patient's MRI, and co-registering it with a neuronavigation system. As an example, a 2 mA anodal tDCS for 20 minutes every day, applied to the left dorsolateral prefrontal cortex (DLPFC), over a period of 5 days, reduces smoking cue-induced craving. The same treatment has been applied to the primary motor cortex contralateral to the somatic painful area of patients with multiple sclerosis, resulting in significant reduction in pain.

Motor function in the paretic hand of chronic stroke patients can improve after a 20 minutes session of tDCS, with 1 mA current; for example, the anode electrode is placed on the scalp over the hand knob area of the primary motor cortex, while the cathode is placed over the contralateral supraorbital region. The same 20 minutes session applied daily, for 5 days, can improve naming performance in stroke patients with aphasia.

Significant improvement in the performance of working memory Parkinson's disease patients may be observed after anodal tDCS was applied to the left DLPFC with a 2 mA current. A 2 mA/20 minutes tDCS applied to the DLPFC daily, over 10 days, can significantly reduce depression score in patients suffering from major depression.

Combining occupational therapy (OT) with cathodaltDCS can lead to motor improvements after stroke; simultaneously with OT, 1 mA cathodaltDCS has been applied in 30 minutes daily sessions, for 5 days, over the contralesional motor region with the reference electrode placed over the contralateral supraorbital region. Applying non-invasive stimulation to brain can cause more effective modulation of the stimulated neural networks, when these networks are pre-activated through behavioral training.

Electrical stimulation applied to the anterior tongue can induce neuromodulation in the balance processing neural networks of patients with vestibular disorders. Stimulation has been applied in 9 sessions, over 5 days, using an array of 144 electrodes, and consisted of bursts of three monophasic square pulses, with a burst frequency of 200 Hz, a pulse frequency of 50 Hz, a voltage of maximum 24V, and a current of under 2 mA.

A significant difference in bioimpedance has been observed between healthy and cancerous tongue tissue, enabling identification and diagnosis of cancerous tissue and other oral conditions. The measurement of bioimpedance allows for screening of oral cancer. By sending a test signal of under 200 mV at 20 Hz and 50 KHz, measuring the response from electrodes placed on the tongue, and searching for significant relative differences in impedance readings (in the range of 1-fold to 3-fold smaller).

With reference to FIG. 1, an overview of the NEAR platform 1 is shown, including the controlling computer 40, the signal driver unit (SDU) 10, connected to an intraoral stimulation board (ISB) 20 by a cable 21, to the external electrode 30 via the wiring 31, and to the controlling computer 40 by a wired or wireless connection 50. The external secondary electrode 30 may be placed on a patient's head or body, and the intraoral stimulation board 20, which has at least one primary electrode, is positioned on the patient's tongue or palate. The signal driver unit 10 is connected to, and provides electrical signals to, the ISB 20 and the external electrode 30 so as to non-invasively communicate an electrical current through the patient's brain between the mouth and the head or body, either from the primary electrode of the ISB 20 to the secondary electrode 30, or from the secondary electrode 30 to the primary electrode of the ISB 20, or bidirectional. The SDU 10 provides a programmable current for treatment to the ISB 20. The SDU 10 receives the details of the treatment program from the controlling computer 40, to which it is connected by a connection 50.

The NEAR platform 1 is a signal generation platform that contains an intraoral stimulation board 20 and external transcutaneous electrodes 30. The NEAR platform is used to non-surgically actuate electrical signals into the brain, in order to achieve neuromodulation and/or sensory augmentation. NEAR can interface bidirectionally with computers 40, utilizing the available on-board sensors, and can apply electrical stimulus in the context of computerized cognitive training. The controlling computer can be an off-the-shelf computer, such as mobile phone, tablet, PC, and so on, known to those skilled in the art. Alternately, the SDU 10 can be programmed to act as a standalone controller box, without the need of a controlling computer; an optional off-the-shelf computer could be used for data storage and display.

Figure 2:
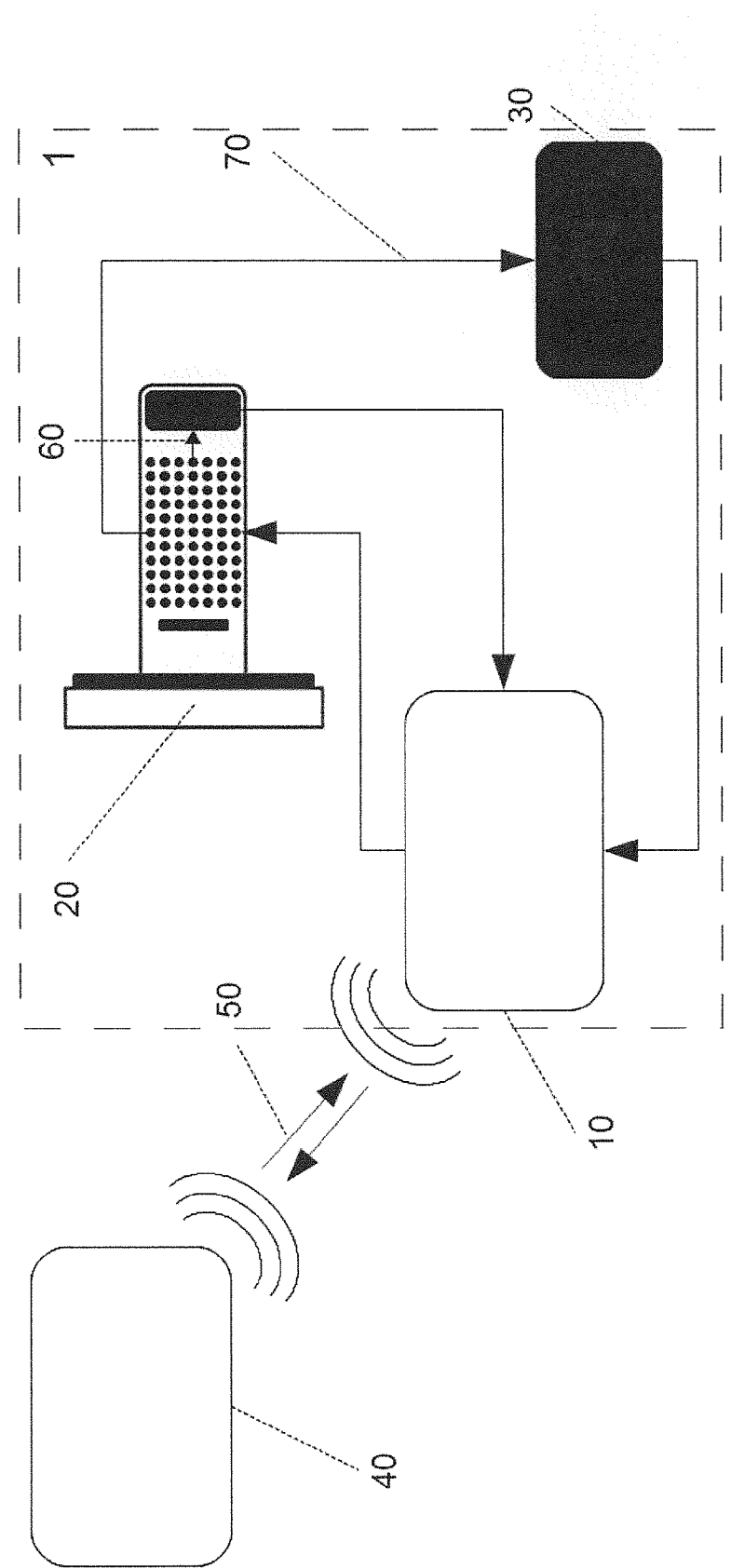
FIG. 2 shows a functional system view showing the components of the NEAR platform.

With reference to FIG. 2, the overall system diagram is shown, with the main components, which are the Signal Driver Unit 10, intraoral stimulation board 20, external electrode(s) 30, and the controlling computer 40 communicating, wired or wireless, with the SDU 10. The controlling computer 40 is running software that coordinates the actions of the SDU 10. This is achieved by sending commands to, and receiving feedback from the SDU 10, via the communication link 50. Based on the commands received from the controlling computer 40, the SDU 10 can start, stop, pause, and resume a stimulation session, and/or read signals from the electrodes 30 and sensors (not shown). In one embodiment multiple external electrodes 30 are used to provide multiple stimulation and return paths, as reference to measure body functions, or to reduce interference when using a wired connection to the controlling computer.

The platform is used to apply electrical signals either via the ISB 20, or via the external electrodes 30, as shown in FIG. 2. The ISB 20 is an electrode array through which electrical signals are applied intraorally (e.g. onto the tongue, palate, etc.). Signals can also be applied across the head or the body (e.g. onto the scalp, arm, etc.) through the external electrodes 30. The platform can apply either an alternating current (AC) or a direct current (DC) signal to the human body. When the stimulation is applied onto the scalp, through the transcutaneous electrodes 30, it is called transcranial stimulation. Transcranial stimulation with DC is referred to as tDCS (transcranial Direct Current Stimulation). The transcranial AC stimulation is referred to as tACS (transcranial Alternating Current Stimulation). The intraoral electrode array 270 is used to apply electrical stimulation to the brain, via the cranial nerves, to apply local stimulus to the tongue, and to receive feedback from the user.

The NEAR device can apply electrical signals with various parameters. The AC output signal parameters that can be altered are frequency, amplitude, duty cycle, and duration. The DC output signal can be modified in amplitude, and duration. These properties of the stimulation signal 180 can be adjusted by the controlling computer 40, via its communication link with the SDU 10.

The ISB 20 is placed into the mouth of the subject in order to apply electrical stimulation the tongue's surface. One or more external electrodes 30 are placed across the head of the subject (also referred to as the user) in an orientation targeting a given brain region. One or more external electrodes 30 can apply signals across the head or the body, while the ISB 20 or other external electrode(s) 30 act as return path. The external electrodes 30 can also sink the current provided by the intraoral electrode array 270 for brain stimulation.

The signal driver unit 10 communicates with a controlling computer 40, which coordinates the treatment sessions, as the user plays interactive games designed for cognitive rehabilitation, or simply receives electrical stimulation for the purpose of treating the respective neurological condition, such as prefrontal cortex damage.

Figure 3:
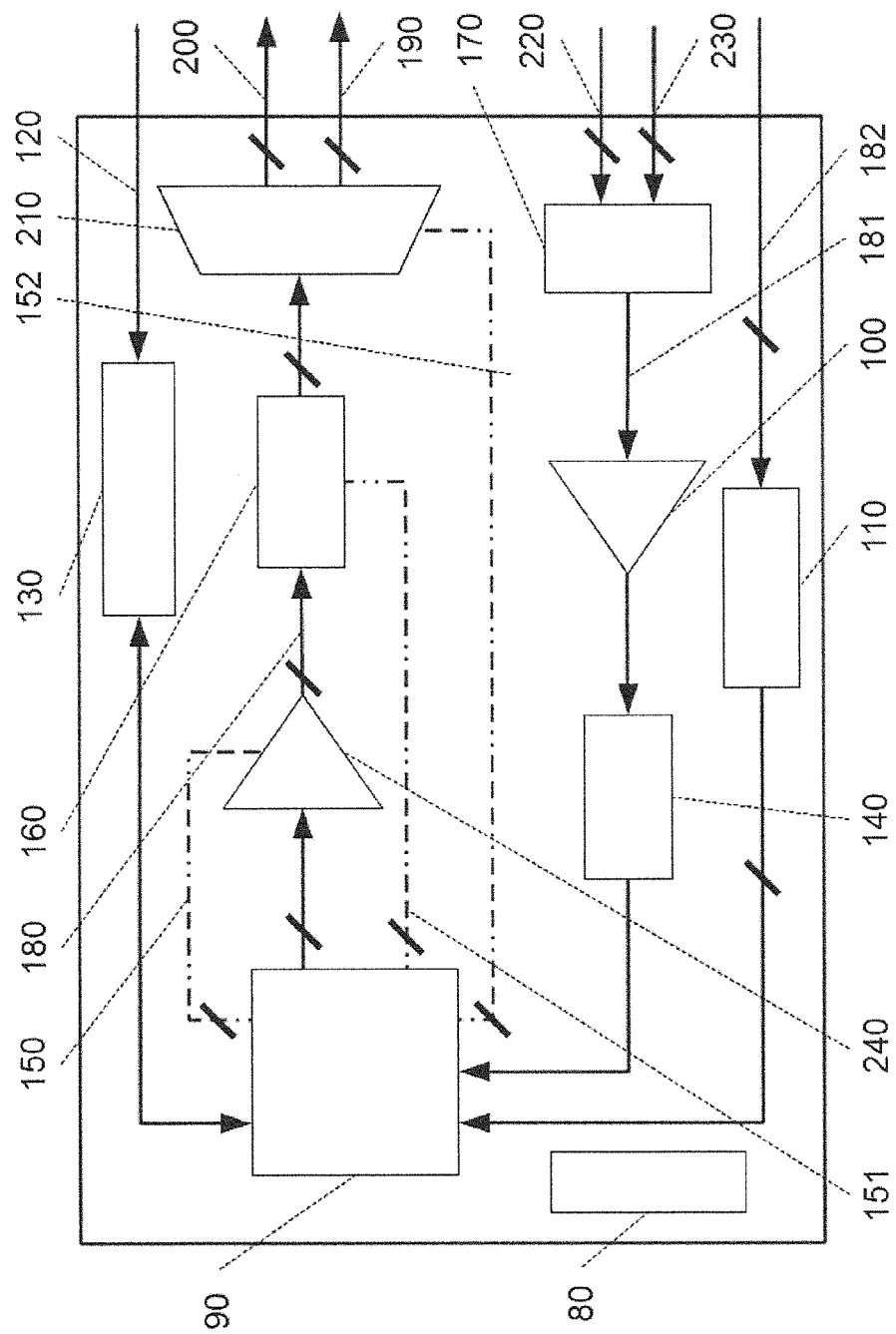
FIG. 3 shows a functional diagram of the signal driver unit of the NEAR platform.

With reference to FIG. 3, an overview of the signal driver unit (SDU) 10 is shown. The NEAR signal driver unit contains a microcontroller unit (MCU) 90, a communication module 130, a power supply 80, a safety module 170, electrode switch fabric 210, signal conditioning modules 110 and 140, a buffer 100, a Digital-to-Analog Converter 240, and an AC converter 160. The continuous lines indicate signal lines and the broken lines represent control lines. On the SDU, a microcontroller 90 actuates a signal, which is then driven by the DAC 240. The AC converter 160 switches the signal to DC or AC mode, and sets the frequency and the polarity of the signal. Next, this signal is put through the electrode switch fabric 210, which provides signals to the electrode array 270 and actuates one or more electrodes 360 at a time. The switch fabric 210 is controlled by the microcontroller 90. A first connector 200 connects to an ISB 20 and a second connector 190 connects to external electrode(s) 30. The switch fabric 210 can be used to drive the external electrode(s) 30, as well as the ISB 20. There are two possible return paths: the first one 220 through the external electrode(s) 30, and a second one through the ISB 20. Also present on the signal driver unit is at least one power supply 80 and a communication module 130 for wired or wireless communications. The communication module 130 provides communication with the controlling computer.

The microcontroller 90 generates the stimulation and the control signals. The stimulation signal is converted by the DAC 240 from digital to analog, and the DAC 240 sets the signal's amplitude based on the control signal 150. Then the signal is routed through the AC converter 160, which drives the DC signal through, or it converts it into AC, based on the control signal 151 received from the microcontroller; the polarity of the signal can also be changed via the control signal 151, to allow for switching between cranial nerve stimulation and transcranial stimulation. From the AC converter, the stimulation signal 180 is routed to the electrode switch fabric 210. The electrode switch fabric 210 selects an output path, either 200 through the ISB, or 190 through the external electrode, based on the control signal 152 received from the microcontroller. The stimulus is routed to the addressed individual electrode in the ISB 20 via 200, by the electrode switch in accordance with the address provided by the microcontroller via the control signal 152.

The safety module 170 monitors the stimulation signal on both return paths, 230 from the ISB 20, and 220 from the external electrode 30. If the current or the voltage of the stimulation signal surpass the safety limit, the stimulation is interrupted, and the microcontroller is sent into a safe state.

The stimulation signal is sampled on the return path, via the buffer 100, for Analog-to-Digital conversion. The amplitude of the sample 181 is rectified and brought into the microcontroller's ADC input range by the signal conditioning module 140.

The microcontroller 90 receives inputs from the controlling computer (not shown) through signal line 120 by means of communications interface 130.

The microcontroller 90 may further receive input 181 from the sensors 320, 330 (shown in FIG. 6) on the ISB 20, through the signal conditioning module 110. The sensors 320, 330 may report user actions, related to Cognitive-Behavioral Training, and other user related information, like the position of the head. Tilting the head or exerting pressure on a sensor could indicate a response from the user, which would then be interpreted by the microcontroller 90, or transmitted to the controlling computer to be analyzed and/or recorded. Cognitive-Behavioral treatment sessions might require the subject to touch certain spots on the ISB 20 in a certain order, or would require the subject to answer certain questions, with "Yes", "No" or "I don't know".

Figure 4:
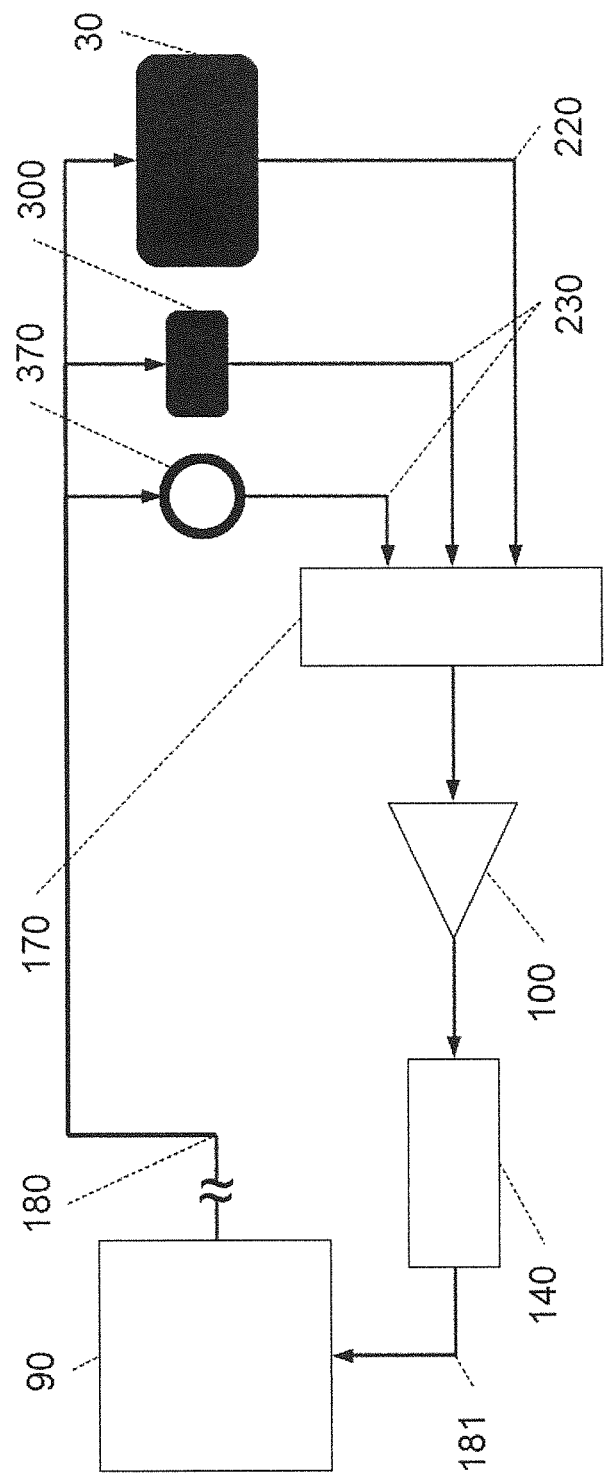
FIG. 4 shows a functional diagram of the electrode feedback circuitry.

With reference to FIG. 4, a functional diagram of the electrode feedback circuitry is shown. By sampling the stimulation signal, the microcontroller receives feedback related to the contact impedance between the intraoral electrodes and tissue, in order to calculate the position of the device relative to the tongue, and to send the stimulation current through the appropriate electrodes on the ISB 20. The signals from electrodes are sampled and conditioned for Analog-to-Digital conversion. The results of the conversion are analyzed by the microcontroller 90 on the SDU 10, in order to map the position of the ISB 20 relative to the tongue.

Figure 5:
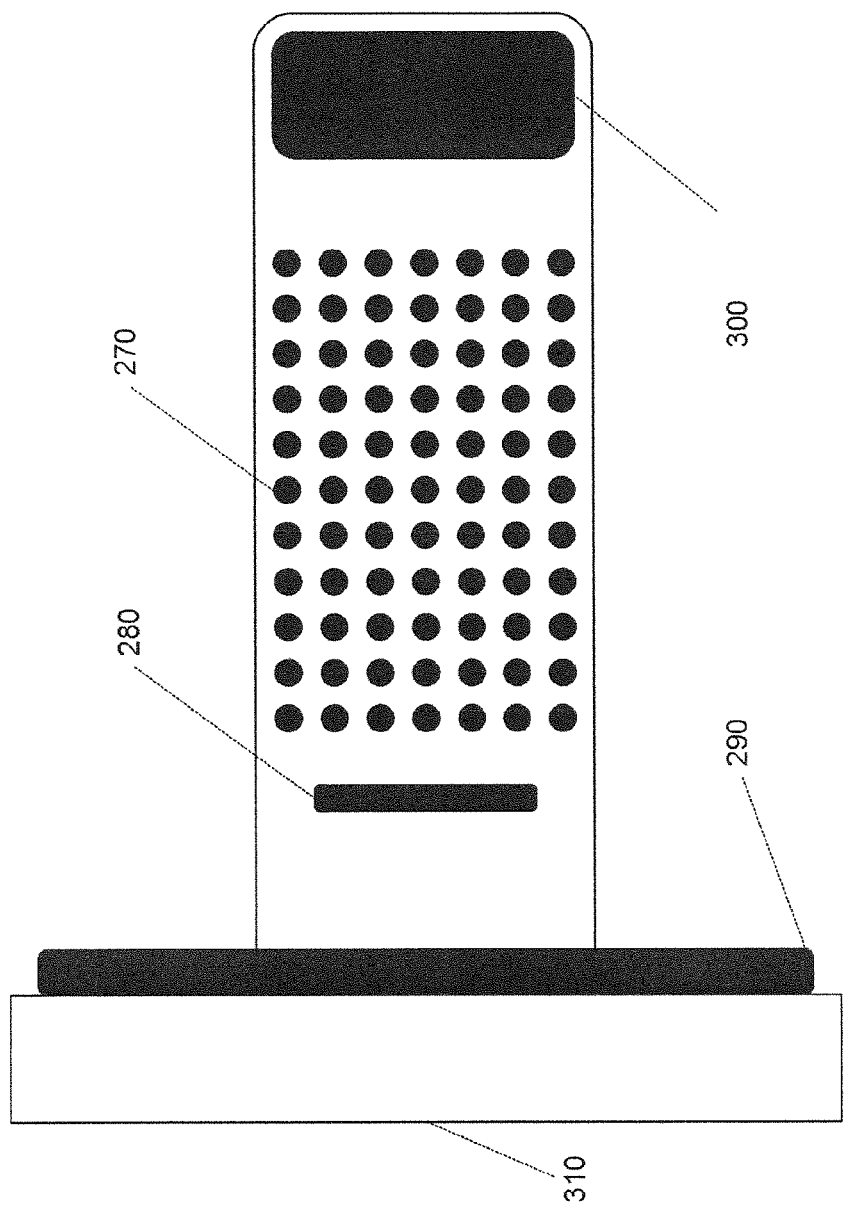
FIG. 5 shows a plan view of the bottom side of the intraoral stimulation device.

With reference to FIG. 5, the bottom view of the ISB 20 is shown with an example 11×7 electrode array, and one return electrode. In an embodiment this is the side that faces a patient's tongue or palate, and can be attached to or encapsulated in a retainer. A M×N array 270 of stimulating primary electrodes 360 is present on one side, having M electrodes across its length and N electrodes across its width. These electrodes 360 can be used to display a pattern, by switching them on and off sequentially, to stimulate certain regions within the oral cavity, or to stimulate the brain in conjunction with one or more external electrodes (not shown). In an embodiment M is 11 and N is 7 as shown however one skilled in the art would appreciate that different numbers of electrodes and different electrode densities are useful for the coverage of the tongue's surface or a better resolution for the actuation of patterns. These electrodes 360 can be used to present an image by stimulating or relaxing the electrodes 360 with the image pattern in sequence (as in an analog CRT display) with the stimulus return referenced to one or more external or ISB electrodes. The ISB 20 has a connector 310 for communication with the SDU by means of a wired or wireless connection.

Figure 6:
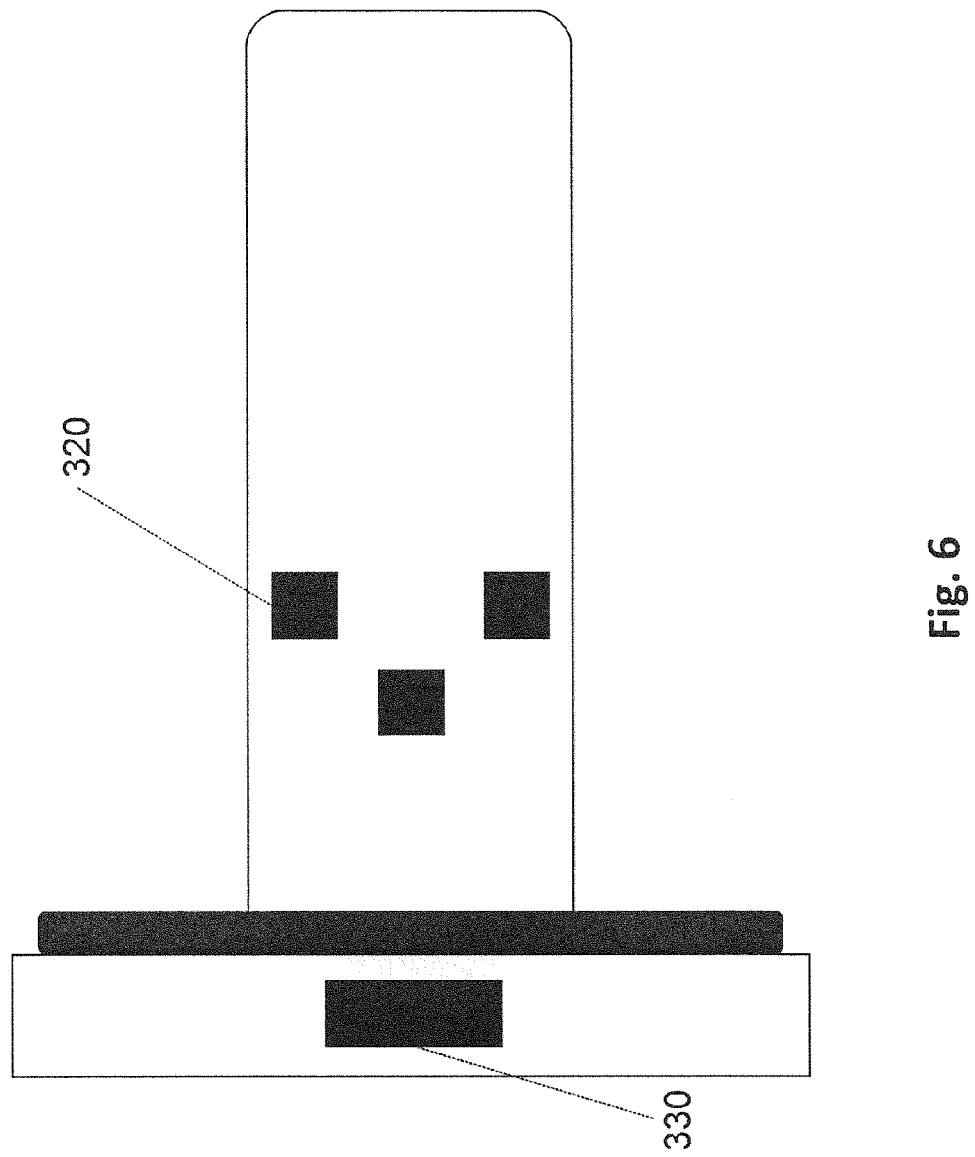
FIG. 6 shows a plan view of the top of the intraoral stimulation device.

With reference to FIG. 6, the top view of the ISB 20 is shown. An accelerometer 330 is used to determine the direction and rate of movement of the ISB 20, and sensors 320 are used to provide feedback from the user to the system. The outputs from the sensors 320 and accelerometer 330 are fed into the SDU 10 and are read by the microcontroller 90. The signals can then be transmitted by the microcontroller 90 to the controlling computer to be interpreted. The sensors 320 can receive input from the user such as right-left or yes-no, for example when the subject's tongue is applying pressure onto the respective sensor. Sensors are supposed to take some feedback/actions from user. Electrodes can be placed on the top of the tongue or on the palate with different types of retainers, provided the electrode array is placed on a flexible board. Sensors 320 can be placed on top of the tongue or on the palate, using different types of retainers (not shown). Preferable embodiments for such a configuration would use a flexible board for housing the array.

The electrode array 360 in the mouth can be used in conjunction with the accelerometer, which provides information on movement of the head, to provide a second user input signal. Therefore there are two input signal pathways, the "mouthpad", and the accelerometer, representing movement on two and three axis respectively. The accelerometer can work in cooperation with the mouthpad to provide further input. In the context of a game, the accelerometer can provide information on where the avatar is looking, and the mouthpad provides directional instructions for the avatar's movement. This is similar to the 2-joystick approach used by the major gaming systems, such as Sony's PS/3™ or Microsoft's XBOX™. This could enable a quadriplegic to play a video game using only his or her head.

Figure 7:
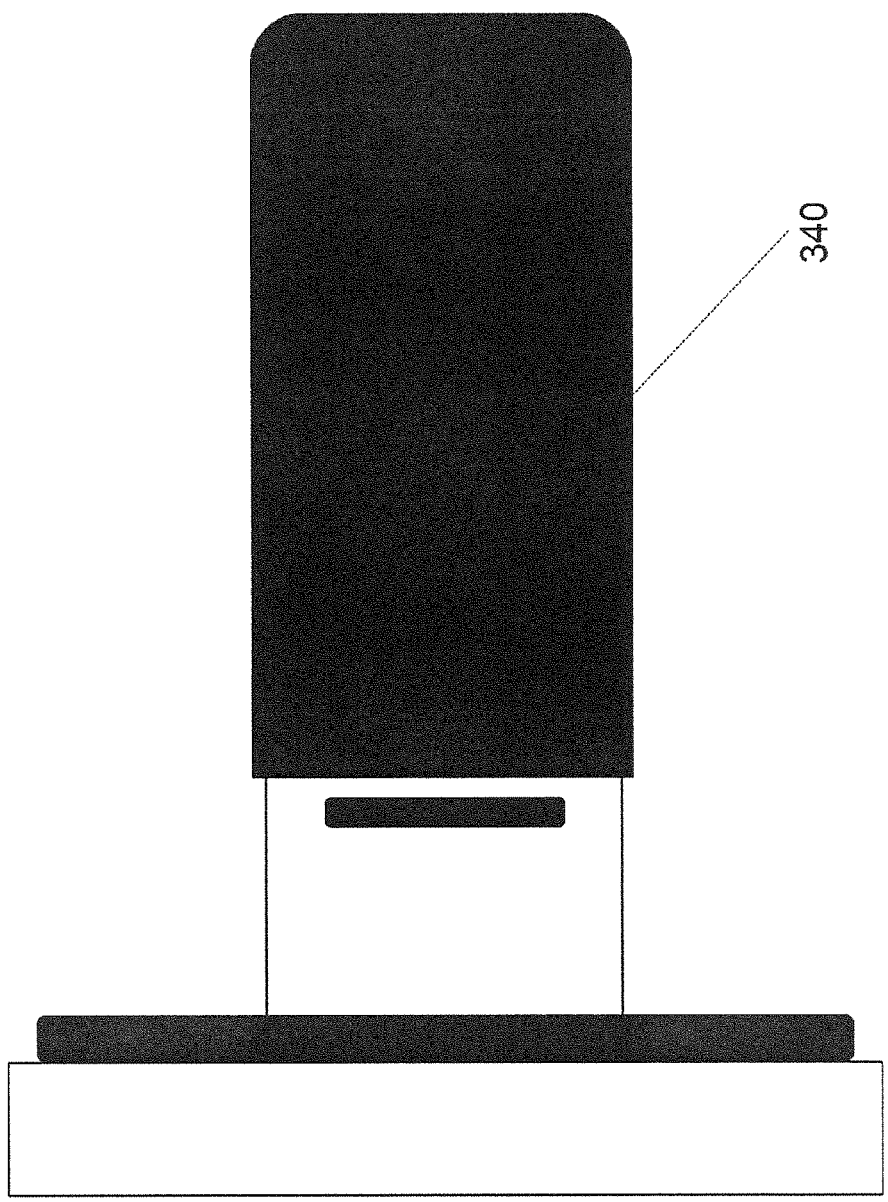
FIG. 7 shows a view of the cover of the intraoral stimulation device.
Figure 8:
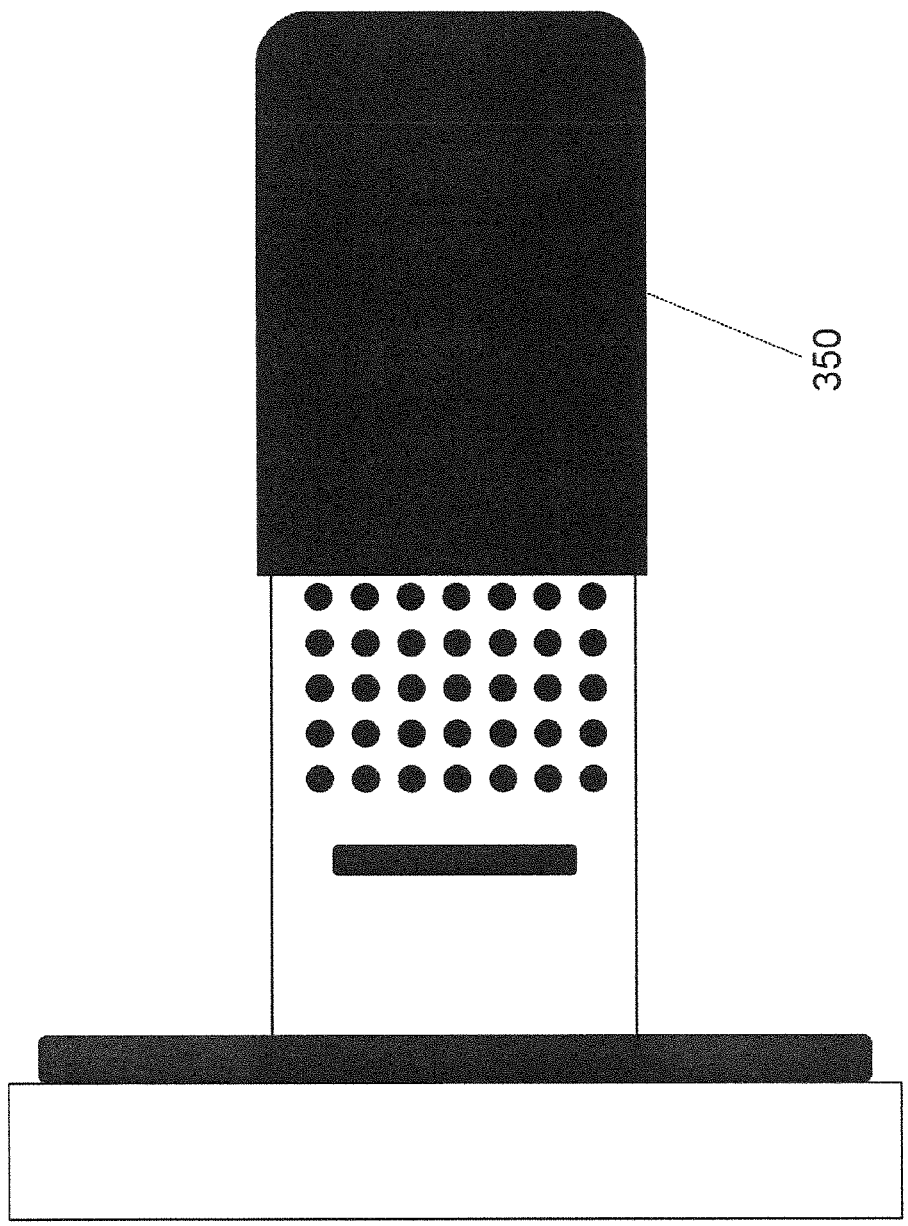
FIG. 8 shows a further view of the cover of the intraoral stimulation device.

In FIGS. 7 and 8, the full conductive cover 340 and the partial conductive cover 350 used for intraoral DC stimulation are presented. DC stimulation requires a physical barrier between the electrode and the body, in order to avoid transfer of material from the electrode into the biological tissue through electrolysis. The primary electrodes 270 of the ISB 20 could provide only DC stimulation when fully covered, in that all normally AC-current electrodes produce a DC current through the presence of the cover, or both AC and DC stimulation when partially covered, such that the covered electrodes communicate DC current and the uncovered primary electrodes communicate AC current. This capability allows for simultaneously applying DC brain stimulation and AC tongue stimulation. The conductive cover could be made from sponge, or alternately it could be made from conductive silicone rubber or other flexible conductive materials known in the art. The partial cover is used when both AC and DC stimulation are used simultaneously. The partial cover has to allow the "widescreen" section of the electrode array to come in contact with the tip of the tongue for AC pattern displaying.

Figure 9:
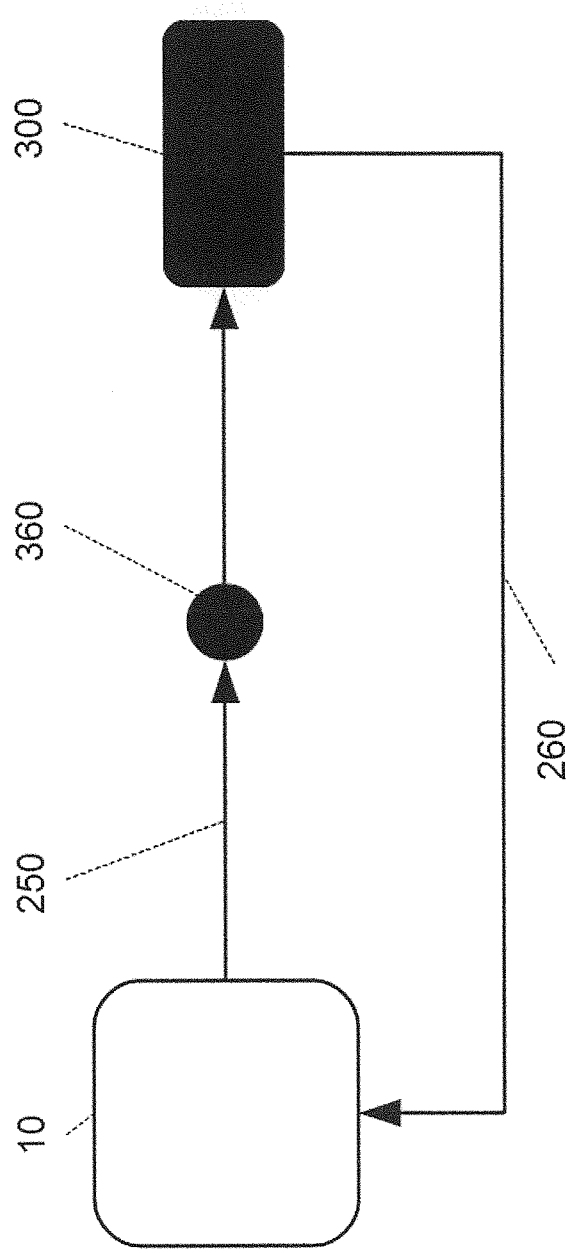
FIG. 9 shows the stimulation signal path when using an intraoral electrode as source and a common intraoral return electrode.
Figure 10:
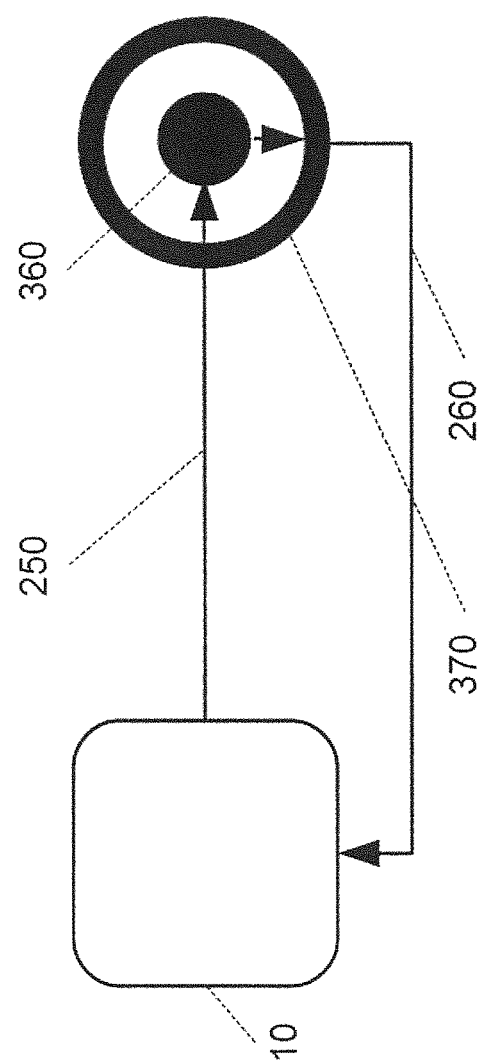
FIG. 10 shows the stimulation signal path when using intraoral return electrodes paired individually with intraoral stimulation electrodes.

With reference to FIGS. 9 and 10, two types of electrode arrays for the ISB 20 are supported by NEAR: one with a common return path for all the electrodes, and another one with individual return paths for each electrode.

For the first type of electrode array, shown in FIG. 9, provides that each electrode 360 has a disk shape and the return path consists of one or more larger electrodes, that can be placed outside the oral cavity, and/or intraorally, on the ISB or elsewhere (e.g. palate, ventral tongue), depending on the application. When stimulating the tongue, the SDU 10 sends the stimulation signal through one or more electrodes 360 by means of the stimulation signal source 250. The respective electrodes act as the source, from where the charge originates, and the return electrode 300 acts as a sink, returning the signal to the SDU 10 by means of the stimulation signal sink 260 to which the signal flows. The drawback to using a common return path is that a larger number of wires are required, which increases the complexity of the electrode switch fabric 210, required for the addressing of individual electrodes. As shown in FIG. 6, sensors 320 that are activated by pressure from the tongue, lips, or teeth, can be placed on the ISB, as can accelerometers 330 that gather data regarding the tilting of the head.

With reference to FIG. 10, the second type of intraoral electrode array provides that each electrode 360 is surrounded by an outer concentric circular metallic sink 370 separated by a gap. The inner disk 360 is the source, from where the signal originates, while the metallic sink 370 is the sink to which the charge flows. One skilled in the art would appreciate that the metallic sink may be in a shape other than circular and still achieve the stated purpose, for example oval, square or amorphous. In a multi-electrode embodiment having rows and columns, such as that shown in FIG. 5, only one row at a time can be active with a signal, and only one column at a time can act as return path. All inactive rows and columns are inactivated by the switch fabric 210. Sending a signal across one row, and then down one column, it will be felt most strongly by the subject where the row and column meet. This approach reduces the number of wires required to drive signals from the NEAR signal driver unit 10. The drawback to this approach is current leakage between adjacent electrodes in the array near the intersection of the activated row and column.

Figure 11:
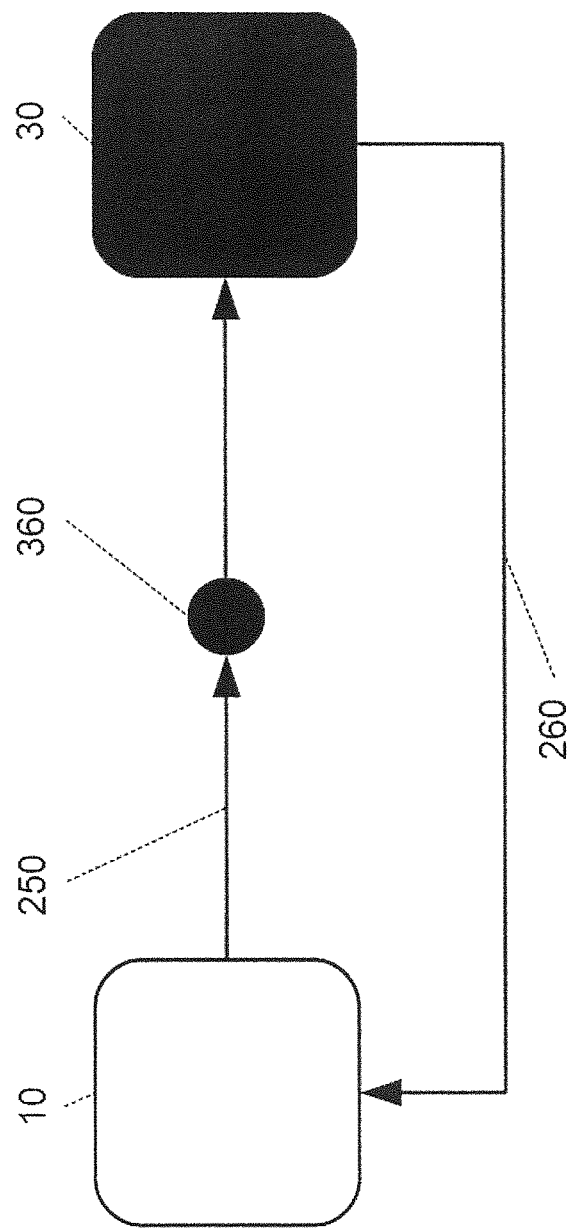
FIG. 11 shows the stimulation signal path when using an intraoral electrode as source and an external return electrode.
Figure 12:
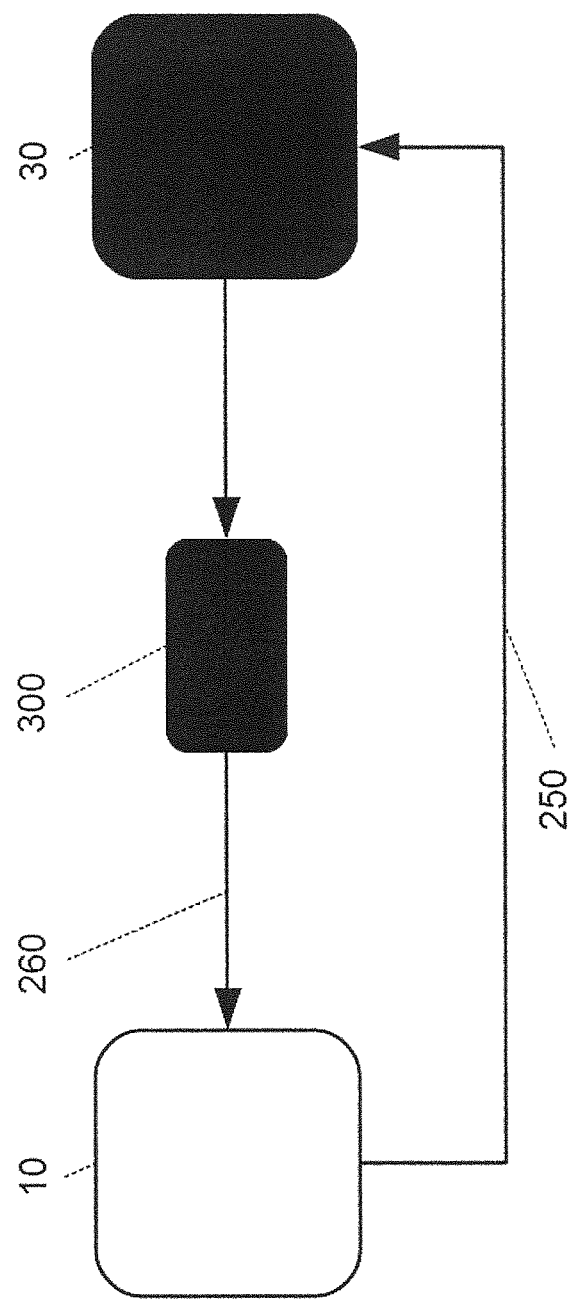
FIG. 12 shows the stimulation signal path when using an external electrode as source and an intraoral return electrode.

With reference to FIGS. 11 and 12, two types of stimulation are shown for Cranial Nerve Stimulation. In the first case shown in FIG. 11, the source is an electrode 360 of the intraoral electrode array 270 (not shown), and the current sinks through one or more external electrodes 30. In the second case shown in FIG. 12, the current direction is inverted by switching the polarity from the AC converter 160 (not shown), such that the one or more external electrodes 30 are the source, while the current sinks through the intraoral common return electrode 300. The CN-NINM treatment may be combined with tDCS treatment such that the two or more electrodes (source and sink) are placed on the patient's head for tDCS treatment, and two or more electrodes (source and sink) are placed in the patient's mouth for CN_NINM treatment, simultaneously.

Figure 13:
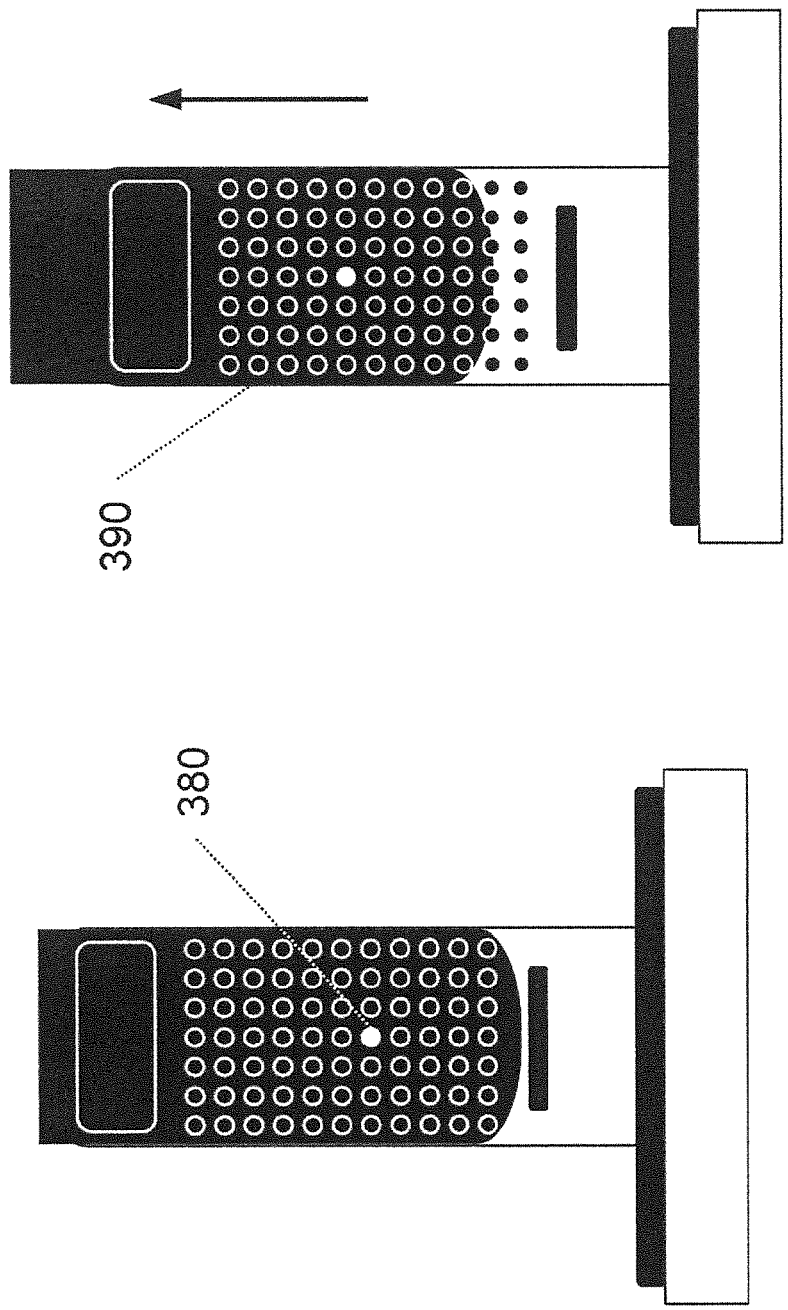
FIG. 13 shows the detection of the tongue's longitudinal position relative to the intraoral stimulation device.
Figure 14:
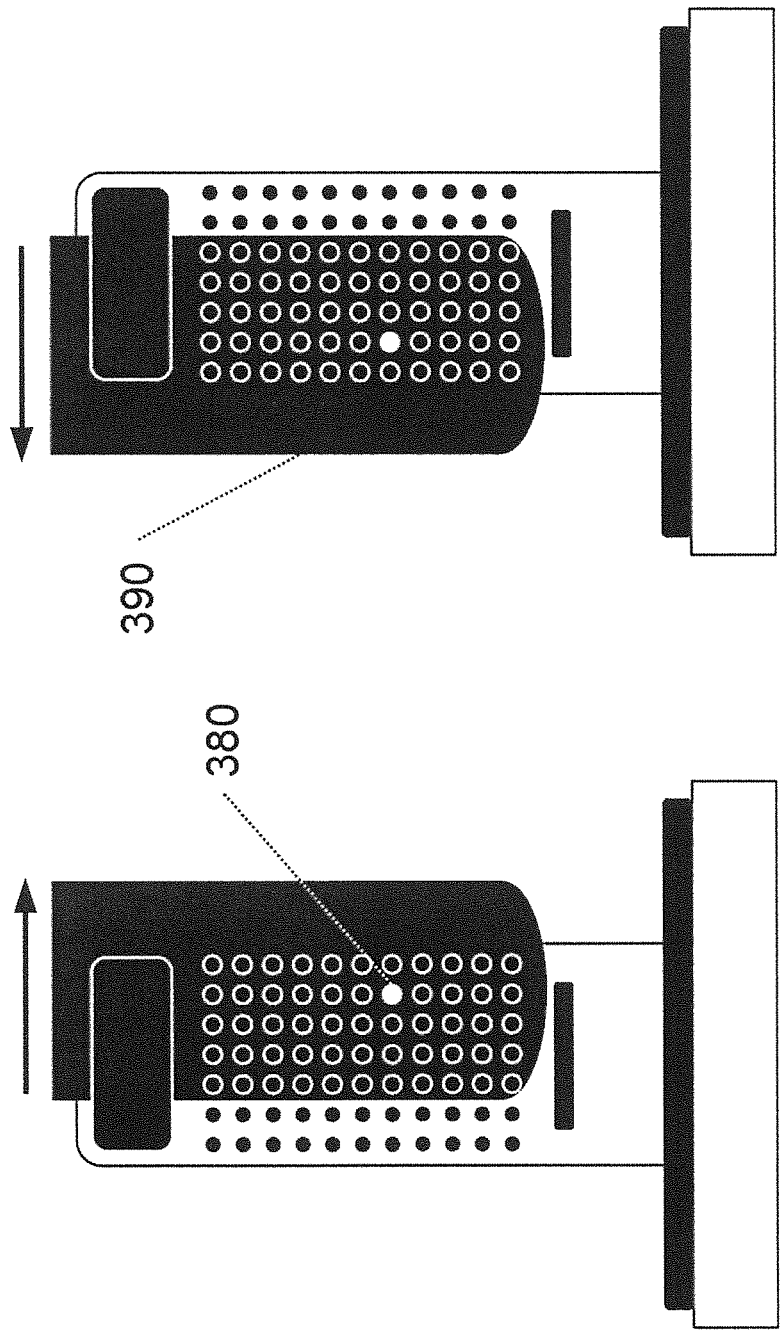
FIG. 14 shows the detection of the tongue's transversal position relative to the intraoral stimulation device.

With reference to FIGS. 13 and 14, the lock-on capability of the device is shown. The NEAR platform 1 is able to lock-on the stimulation to a predetermined position on the tongue 370, by monitoring the relative position of the device against the tongue 370. This is achieved by constantly monitoring the position of the ISB 20 relative to the subject's tongue 370, as described in FIG. 4. When the ISB 20 changes its position; the SDU 10 switches the output over to another electrode to compensate for the change in position; when the offset between the ISB 20 and the tongue 370 becomes too large to compensate, the SDU pauses the stimulation and signals the problem to the human operator.

The NEAR platform 1 has the capability of locking the stimulation signal onto a previously mapped intraoral location, for example a specific location on the tongue in an embodiment, as shown in FIGS. 13 and 14. The contact impedance of the intraoral electrodes, read by the MCU 90 via feedback circuitry as shown in FIG. 4, provides a contact map for the intraoral electrode array 270. After a first calibration, when all the electrodes are in contact with the tongue, the relative position of the active stimulation electrode 380 is stored in memory, and then is checked periodically during the stimulation session, against the contact map, and readjusted if necessary. The adjustment of the stimulation point in the case of lateral move is shown in FIG. 14. The adjustment in the case of longitudinal movement is shown in FIG. 13; the longitudinal movement of the tongue is only possible inwards, since the tongue guide 280 prevents the tongue from moving outwards. Improved contact between the tongue and the ISB can be insured with the help of a dental retainer (not shown), which prevents the vertical movement of the tongue, and allows for good contact with the intraoral electrodes, as well as an easier way to provide feedback via the sensors mounted on the top side of the ISB 20.

Figure 15:
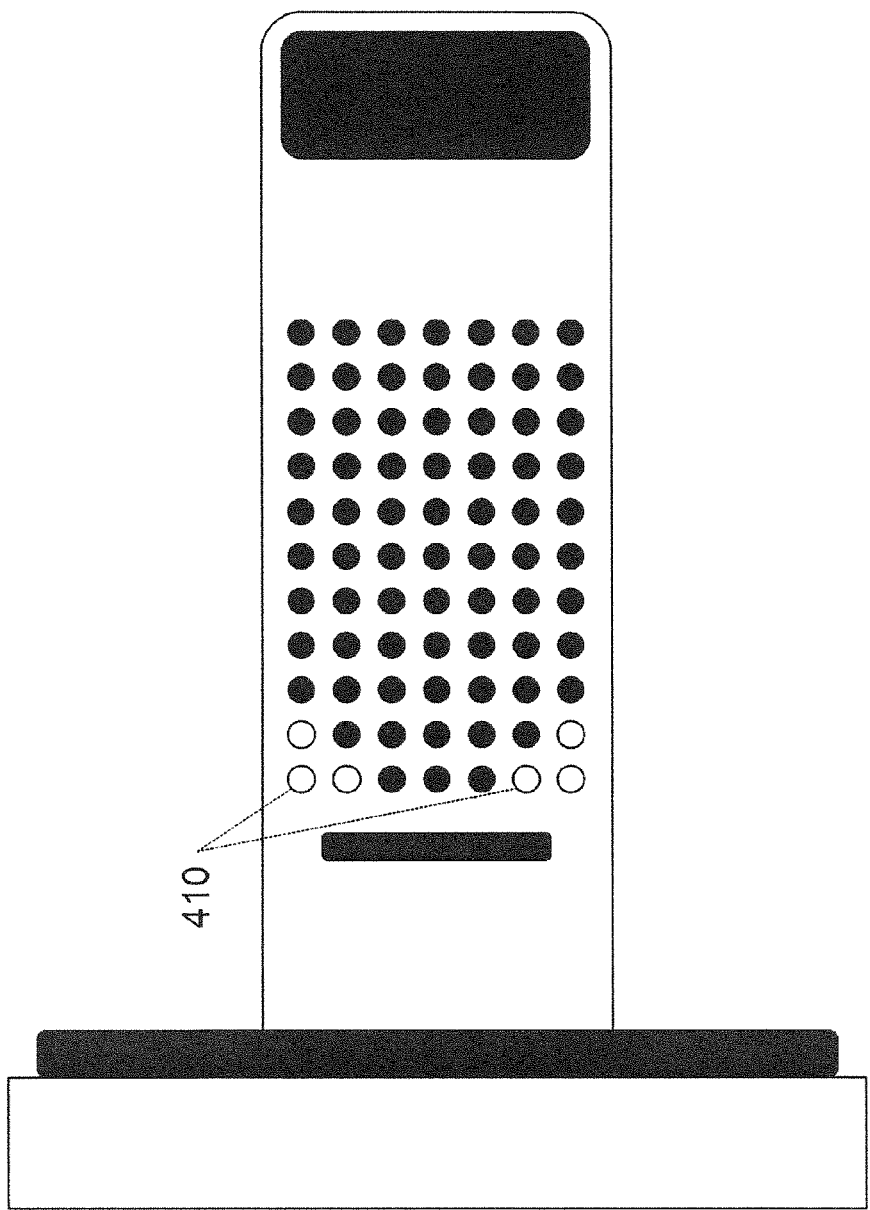
FIG. 15 shows the use of a subset of electrodes from the intraoral electrode array.

With reference to FIG. 15, the use of a subset of the intraoral electrodes 360 is shown. The tongue's sensitivity to current is related to the taste bud density. It is known that the tip of the tongue is more sensitive than the posterior region with an approximate perception ratio of 2:1. To maximize perception, the platform provides the stimulation signal via a subset of the electrodes that are placed against the tip of the tongue. Other factors influence the tongue's electrical sensitivity as well. One of them is adaptation, which can be avoided partially or entirely by constantly manipulating the properties of the applied electrical signal, like frequency, and duty cycle. Another factor to the electrical sensitivity of the tongue is age. Elderly people experience a reduction in taste buds, and thus weakened electrical sensitivity on the tip of the tongue. In fact, in the elderly, the threshold sensitivity at the tip of the tongue is similar to the posterior surface of the tongue in young persons. The platform has the capability of adjusting the stimulation to adapt to higher or lower sensitivity thresholds, by adjusting the electrical properties of the signal via the DAC 240 and the AC converter 160.

By using a specific subset of the intraoral electrode array 270, the platform is capable to optimize the pattern display by actuating the pattern onto the most sensitive region of the tongue: the anterior third. A preliminary calibration can be performed in order to detect the depth of the sensitive region and the number of electrodes needed to provide the stimulation, as well as the optimal stimulation level. One electrode, located at the tip of the tongue—in the middle of the first row, is activated individually for a calibration cycle. The cycle consists of incrementing the amplitude of the signal from minimum towards maximum, while decrementing the frequency from maximum towards minimum, until the desired level of stimulation is achieved. A sensitivity map is built for the respective subject, by testing the rest of the electrodes with the optimal signal, and then comparing them against the first electrode. The sensitivity map is used to select the reduced set of electrodes to be used for pattern recognition. The reduced set of electrodes will be left uncovered when using the conductive cover, and they make up the "widescreen" format. The "widescreen" allows for better perception of patterns by the brain as it corresponds to the natural vision format.

Figure 16:
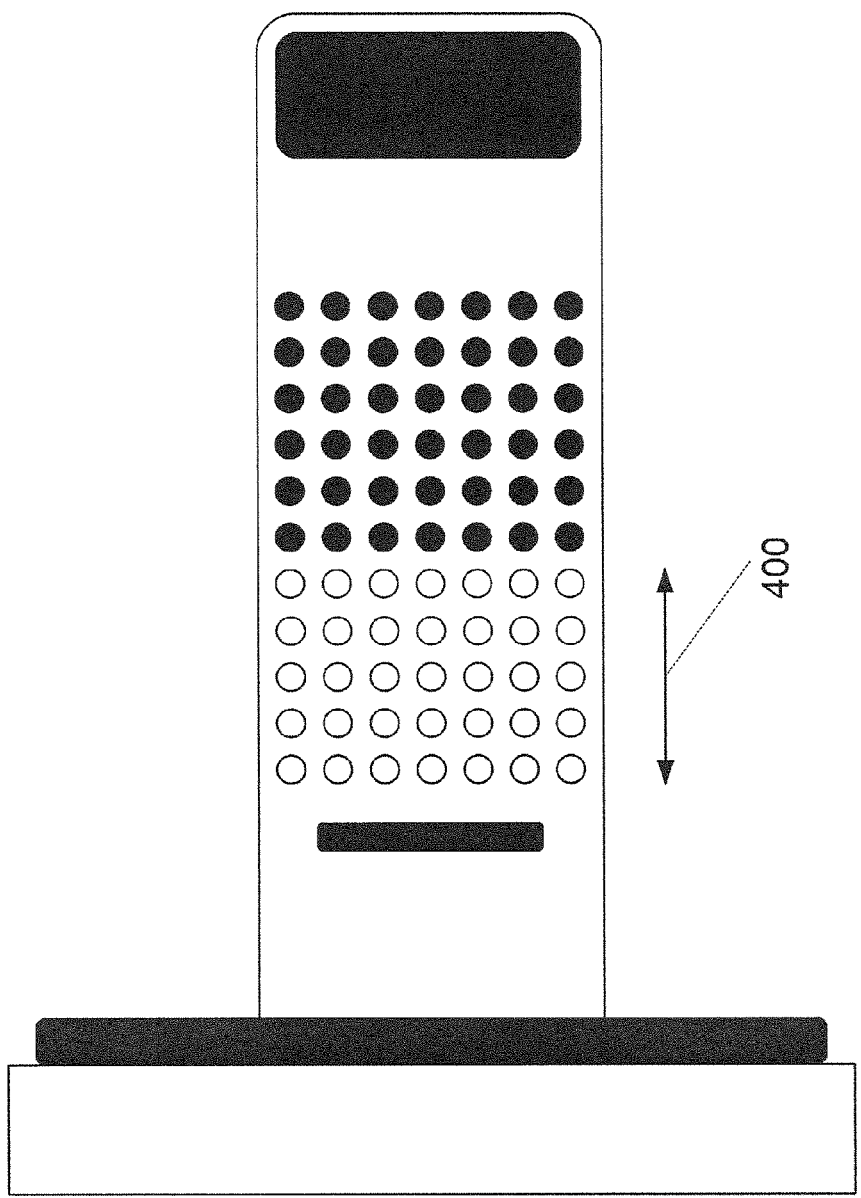
FIG. 16 shows the use of a subset of electrodes from the intraoral electrode array as special functions, while using the ISB as "mouthpad".

With reference to FIGS. 15 and 16, the electrode array may be operated as a touchpad, called "mouthpad" in this context. The tip of the tongue is used as a pointing device, its position being determined by the impedance of the contact between the tongue and the electrode array, on an active section 400 of the intraoral electrode array. The tip of the tongue may engage in several movements on the array, such as a "swipe" in one direction to scroll the screen or move a figure in that direction, or a "double click" wherein the tongue touches twice within a short period of time to select an object on the screen, for instance. Furthermore, sensors 320 may be used as "mouse buttons", or alternately, certain predetermined sections 410 of the electrode array may be designated as "buttons" or have specific functions like "scroll", as shown in FIG. 6. This input provides information regarding user actions on a two-dimensional plane such as a screen.

Novel Methods Using the NEAR Platform

The platform is able to provide non invasive brain electrical stimulation via the cranial nerves, with or without external return path, as well as transcranial electrical stimulation, with both AC and DC signals. Cranial Nerve Stimulation, Transcranial Direct Current Stimulation, and Transcranial Alternating Current Stimulation can be provided stand alone, or combined. For example, CNES can be provided by sending an electrical current through the oral cavity, via the ISB 20, into the brain and sinking it through an external transcutaneous electrode 30, placed on the head or body.

The NEAR platform 1 is aware of the ISB's 20 position, relative to the stimulation site, and is able to lock-on the stimulation to a predetermined point, based on the impedance mapping of the contacts between the intraoral electrode array and the surface of the stimulated region. This can be achieved by sending a test signal via the intraoral electrode array, and sampling it on the return path. The drop in the signal is then used to create a contact map, based on a threshold obtained experimentally.

Early diagnosis of oral conditions, like oral cancer, can be provided by detecting low impedance tissue regions; low impedance is known to characterize cancerous tissue. The impedance is calculated based on the data used in the mapping of the contacts between electrodes and the tissue.

The characteristics of the signal outputted by the ISB 20 are adjustable. The characteristics of the signal can be calibrated for each subject, based on their individual physiology and level of sensitivity; the calibration can be done for one or more electrodes.

Although the invention has been described above by reference to certain embodiments of the invention, the invention is not limited to the embodiments described above. Modifications and variations of the embodiments described above will occur to those skilled in the art in light of the above teachings. Moreover, with respect to the above description, it is to be understood that the optimum dimensional relationships for the component members of the present invention may include variations in size, material, shape, form, funding and manner of operation.

We claim:

1. A device for cranial nerve stimulation of an individual, the device comprising:

a signal driver unit for providing both AC and DC current;

an intraoral stimulation board having at least one primary electrode for the AC current and at least one primary electrode for the DC current, the respective primary electrodes being configured for communicating the respective currents with the tongue of the individual, the intraoral stimulation board connected to the signal driver unit;

at least one secondary electrode configured to be positioned on the cranium of the individual for communicating either the AC or DC current through the brain of the individual, the at least one secondary electrode connected to the signal driver unit, wherein either the AC or DC current can flow between the intraoral stimulation board and the at least one secondary electrode to apply transcranial current stimulation; and a partial conductive cover that covers part of the intraoral stimulation board for preventing deposition of electrode materials onto the tongue when direct current is applied, wherein the AC current is provided by the at least one primary electrode that is uncovered, and the DC current is communicated by the at least one primary electrode that is covered, and wherein the AC current and DC current are communicated simultaneously.

2. The device of claim 1 further comprising:

a microcontroller connected to the primary and secondary electrodes, the microcontroller comprising an Analog-to-Digital Conversion module;

a feedback loop between the electrodes and the microcontroller, wherein the signal driver sends a test signal between the primary and secondary electrodes, wherein said Analog-to-Digital Conversion module of the microcontroller measures the test signal; and one or more multiplexers to actuate selected primary electrodes.

3. The device of claim 2 wherein each electrode comprises an inner electrode and an outer electrode, and wherein the microcontroller determines a tongue position by measuring an impedance between the inner electrode and the outer electrode of each electrode, wherein the device is operable as a pointing device.

4. The device of claim 3, wherein each inner electrode is a source and each outer electrode is a sink.

5. The device of claim 3, wherein each inner electrode is a sink and each outer electrode is a source.

6. The device of claim 2 wherein selected electrodes operate as mouse buttons for a pointing device by providing a signal to the microcontroller.

7. The device of claim 2 further comprising predetermined sections of the electrodes, wherein each section represents an action such that activating a section triggers the microcontroller to perform the representative action.

8. The device of claim 2, further comprising sensors that operate as mouse buttons for a pointing device by providing a signal to the microcontroller.

9. The device of claim 2 wherein the microcontroller calculates the position of the device relative to the tongue and sends the stimulation current through certain electrodes based on the position of the device.

* * * * *